United States Patent [19]

Rydell

[11] 4,174,417

[45] Nov. 13, 1979

[54] METHOD OF FORMING HIGHLY ABSORBENT FIBROUS WEBS AND RESULTING PRODUCTS

[75] Inventor: Theodore B. Rydell, Neenah, Wis.

[73] Assignee: Kimberly-Clark Corporation, Neenah, Wis.

[21] Appl. No.: 861,721

[22] Filed: Dec. 19, 1977

Related U.S. Application Data

[63] Continuation-in-part of Ser. No. 621,840, Oct. 14, 1975, abandoned.

[51] Int. Cl.² .............................................. B32B 23/02
[52] U.S. Cl. ..................................... 428/221; 156/290; 162/157 C; 264/115; 264/121; 264/207; 428/283; 428/364; 428/910
[58] Field of Search ............................... 128/284, 296; 162/157 C, 213; 264/115, 121, 207; 260/17.4 GC, 17.4 ST, 17.4 CL; 156/290; 428/221, 283, 364, 910

[56] References Cited

U.S. PATENT DOCUMENTS

| | | | |
|---|---|---|---|
| 3,046,078 | 7/1962 | Salsburg | 260/17.4 GC |
| 3,065,041 | 11/1962 | Sven | 8/116 R |
| 3,194,727 | 7/1965 | Adams et al. | 8/157 C |
| 3,455,643 | 7/1969 | Gruber et al. | 8/116 R |
| 3,589,364 | 6/1971 | Dean et al. | 162/146 |
| 3,658,790 | 4/1972 | Bernardin | 260/219 |
| 3,670,679 | 6/1972 | Mitchell | 112/10 |
| 3,691,154 | 9/1972 | Bernardin | 128/285 |
| 3,997,647 | 12/1976 | Lassen | 428/393 |

*Primary Examiner*—James J. Bell
*Attorney, Agent, or Firm*—Daniel J. Hanlon, Jr.; William D. Herrick; R. J. Miller

[57] ABSTRACT

Webs are formed by mixing chemically modified cellulose fibers in a carrier and dewatering to form a mixture of gel-like consistency having a minimum of external water wherein the fibers have not lost their individual structures. This mixture is sprayed or injected into a gas stream of volume and velocity such that the individual fibers are separated. These fibers are collected into highly-absorbent webs having varying structures. Due to the rapid separation of fibers and subsequent drying, reduced interfiber hydrogen bonding takes place resulting in good tactile properties such as softness and drape. By controlling the direction and velocity of the fibers, webs can be produced having structures ranging from very dense mats to loose, fluffy batt-like products. The webs of the invention possess high absorbency, good wicking, and strength sufficient for handling. They may be used as components for wipers, surgical sponges, and personal care products such as sanitary napkins, tampons, and disposable diapers.

14 Claims, 28 Drawing Figures

METHOD OF FORMING HIGHLY ABSORBENT FIBROUS WEBS AND RESULTING PRODUCTS

REFERENCE TO RELATED APPLICATIONS

This is a continuation-in-part of copending application Ser. No. 621,840 filed Oct. 14, 1975, and now abandoned.

BACKGROUND OF THE INVENTION

1. Field of the Invention

This invention relates to highly-absorbent webs and methods of making them. More specifically it pertains to an improved process of forming such webs of chemically modified cellulose fibers that are not only highly-absorbent but have excellent tactile properties such as softness and drape. Such webs have adequate strength and controlled wicking properties making them particularly suitable as a component of products where it is desirable to draw liquids away from the surface and concentrate them in a particular area or location. Such applications include, by way of example and not limitation, disposable diapers, sanitary napkins, tampons, wipers, surgical sponges, and the like.

2. Description of the Prior Art

The chemical modification of cellulose to increase its absorbency has been previously described and can be considered in a broad sense to fall into three major classifications in terms of methods:

(a) chemical substitution, etherization or esterification;
(b) chemical substitution plus crosslinking; and
(c) polymeric grafting.

For example, U.S. Pat. No. 3,670,679 to Mitchell is directed to absorbent fibers formed by extruding solutions such as those prepared from a hydroxyalkyl cellulose. As examples of category "(a)" above, Bernardin U.S. Pat. Nos. 3,658,790 and 3,691,154 disclose absorbent fibers in batt-like mats formed from phosphorylated cellulose or its acid form and products incorporating them. An example of category "(b)" above is disclosed in U.S. Pat. No. 3,589,364 to Dean et al which discloses absorbent structures including crosslinked fibers of carboxymethyl cellulose and products made therefrom. Category "(c)" above is exemplified by the formation of acrylonitrile grafted cellulose absorbent fibers and products as disclosed in U.S. Pat. Nos. 3,194,727 to Adams et al; 3,455,643 to Gruber et al; 3,065,041 to Sven; and 3,046,078 to Salsbury.

U.S. Pat. No. 3,997,647 to Lassen, assigned to the assignee of the present invention, discloses an extrusion process for forming highly-absorbent filamentary webs from gel-like extrudates. These extrudates include swollen fibers of chemically modified cellulose which have not lost their individual identities. By extrusion the fibers are aligned and interbonded to form filaments having channels and capillaries which provide high absorbency and excellent wicking properties. However, the interfiber bonding, believed to be hydrogen bonding, produced by the method of the Lassen patent tends to produce a harsh, stiff web unless solvent drying or other special drying means are employed. Solvent drying is, of course, relatively expensive in terms of operating costs as well as capital investment required for recovery equipment. In addition, the use of solvents requires precautions to be taken against ecological, safety and health hazards.

SUMMARY OF THE INVENTION

The present invention is directed to an improved method for forming soft, drapable, highly-absorbent webs of chemically modified fibers without the need for solvent drying. In accordance with the present invention the chemically modified cellulose fibers are mixed with the imbibed solvent and dewatered to form a gel-like mixture having a minimum of external water that is sprayed or injected into a gas stream, usually air. The velocity and direction of the air stream are controlled so that the individual fibers are separated and can be collected fo form an open, lightly bonded web. In this manner interfiber bonding is, in the subsequent drying process, minimized and a soft, drapable web results. The density of the web may be controlled by external water content and, by varying the degree of fiber drying and the fiber velocity. Webs may be produced having a wide variety of structures from close, compact fibers to loose, open webs and a wide range of properties including absorbency and wicking rates. Increased drying rates may be obtained by high energy applications, such as heated air or microwaves.

Preferred forms of chemically modified fibers include phosphorylated cellulose, crosslinked carboxymethyl cellulose, and acrylonitrile grafted cellulose. These fibers may be used alone to form highly absorbent webs or to enhance the properties of other fibrous webs by admixture therewith. Formed structures may be produced by directing the air stream onto molds, and laminates with reinforcing scrims or other films or fabrics can be constructed by appropriate application of the fibrous air stream in accordance with the invention.

The webs of the present invention find particular applicability in improving the performance of absorbent products such as wipers, surgical sponges, sanitary napkins, tampons, disposable diapers, and the like.

DESCRIPTION OF THE PREFERRED EMBODIMENTS

Figure 1:
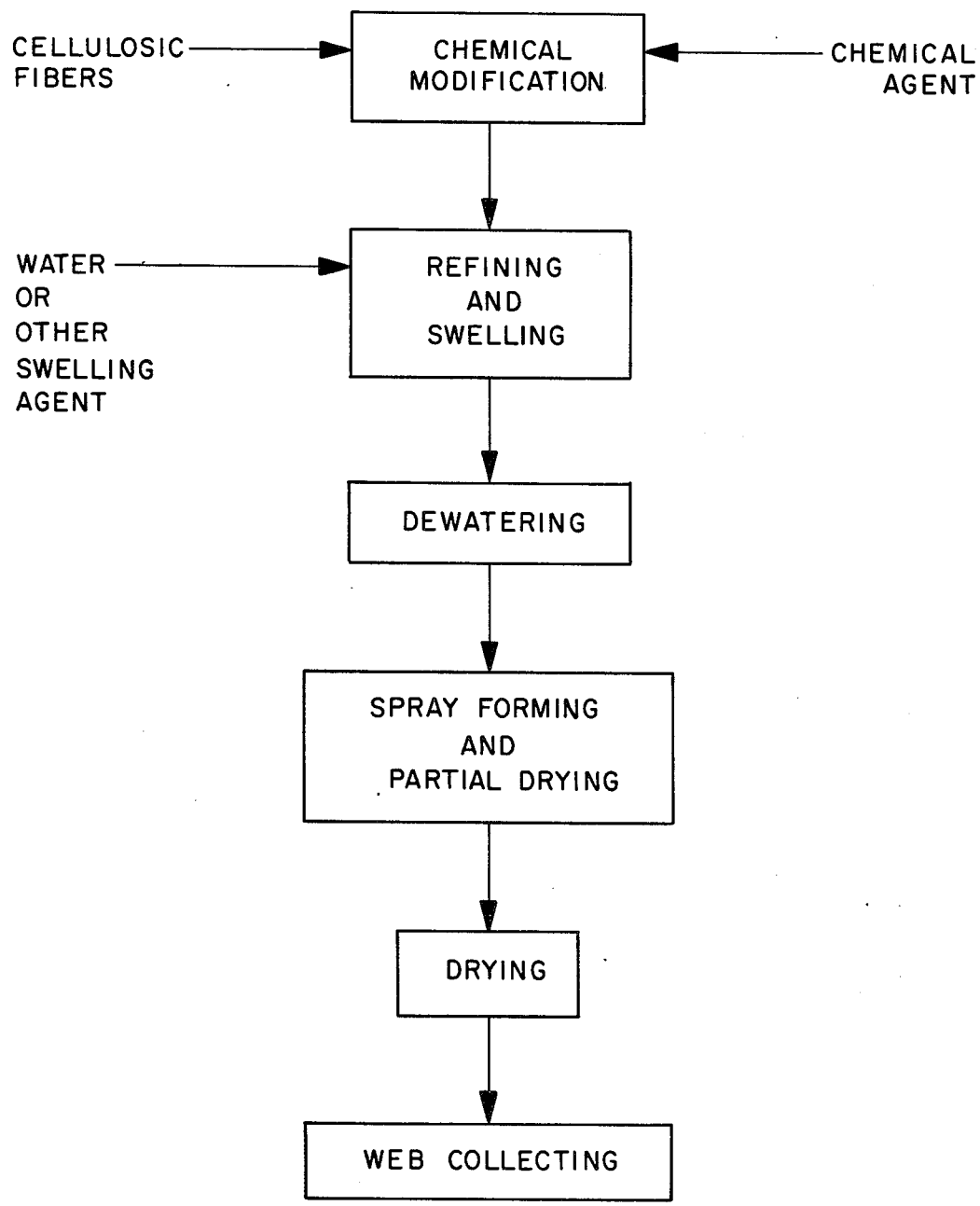
FIG. 1 is a flow chart illustrating the process of the present invention.

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

In order to provide a complete understanding of the present invention, the intended meaning of certain terms used within the description will be stated:

"Chemically modified cellulose" refers to cellulosic materials, the composition and/or structures of which have been transformed by derivatization in such a way as to induce a significant increase in their hydrophilic character. Examples of derivatization processes include carboxylation, phosphorylation, and grafting of acrylic segments. The present invention is not concerned with cellulosic solutions or other cellulosic compositions in which the individual fibers or other basic structures, themselves, lose their identity;

"Highly absorbent" as used herein indicates that the modified cellulose will absorb significantly more of the liquid being used than will unmodified cellulose under the same conditions. It is recognized that the particular absorbency rating will depend not only on the specific material tested but on the conditions under which the measurements are made. For example, the absorbency of a material under pressure may be quite different from its absorbency in an uncompressed state;

"Fibers" is used herein in reference to the fibers of chemically modified cellulose that are mixed with a swelling solvent to form the mixture used in the process of the invention; for cost considerations the fibers generally have a length preferably of about papermaking fiber size, e.g., about 0.02 to 0.2 inches and a diameter preferably about 0.002 to 0.003 inches although larger fibers such as cotton linters may be used.

"Water retention" is defined in U.S. Pat. No. 3,670,069 to Mitchell et al, at column 6, lines 51 to 70, as the moisture remaining in and on a rewet fiber specimen after it has been centrifuged 10 minutes at an acceleration of 1000 times normal gravitational acceleration. For most practical purposes, this will be substantially equivalent to the "Fiber Saturation Point" as later defined;

"Free standing saline absorbency" is a measure of the normal saline capacity under zero load. It is determined by first placing a preweighed sample in 1 normal saline solution for 30 seconds. The sample is then removed with a spatula, allowed to drip for 30 seconds and weighed again wet. The saline picked up divided by the original dry sample weight is the free standing saline absorbency;

"Wicking" is determined by placing a sample over concentric conductive rings which are fixed 1-1/16 inches apart radially. Current is applied and liquid added to the center of the rings at a rate of 240 milliliters per minute. When the liquid reaches the outer ring, the circuit is completed, and this time is reported as the wicking rate. This test is further described in the above-referenced Lassen patent;

"Tensile" was measured using a Model TM-M Instron Tensile Tester equipped with a "B" cell and operated on a sample two inches wide with a jaw separation of ¼ inch, a crosshead speed of ½ inch per minute, a full scale load range of from 1000 grams to 10,000 grams and a chart speed of 5 centimeters per minute. Wet tensile results were obtained in the same manner on samples soaked for 30 seconds in 1 normal saline prior to testing;

"Breaking length" results were obtained as follows:

$$\text{Breaking length (meters)} = \frac{\text{tensile (g/cm)}}{\text{basis weight (g/cm}^2\text{)}} \times \frac{1}{100}$$

"Extrudate" refers to a mass of extrudable, hydrophilic, fibrous cellulosic material which has been swollen by the imbibition of a solvent to such an extent as to plasticize the individual cellulosic fibers and render them independently mobile. In all cases, external water content is preferably minimized and doses not exceed a range of ±5 g/g fiber of the fiber saturation point.

"Dry fiber consistency" as used herein means weight percent of dry fibrous material. Dry weight is determined by drying samples for 2 hours at 105° C. in any of the compositions or mixtures recited. All percentages are by weight unless otherwise noted.

In the process of the present invention as illustrated in FIG. 1, the first step is to provide chemically modified cellulose fibers. While commercially available products such as "Buckeye" carboxylated cellulose from Buckeye Corporation, for example, with modification, may be useful in this process, the diversity of results which may be obtained is increased by beginning with pulp or wood fibers and treating them by phosphorylation, carboxylation, or acrylonitrile substitution as set forth in greater detail below.

One of the preferred types of chemically modified fibers for use in the present invention is phosphorylated pulp fibers. To produce such fibers the following process may be used although it will be recognized by those skilled in this art that variations and modifications of this phosphorylation process may also be utilized.

The particular pulp selected to be phosphorylated is not critical; for example, Northern spruce pulp is readily available, generally low in cost, and produces very acceptable results. The pulp may be used in dry sheet form as supplied by pulp manufacturers. The sheets are preferably immersed for about 15 to 45 minutes in a reagent composition containing about 50% urea and about 32% phosphoric acid, for example. The purpose of this immersion is to distribute those reagents evenly throughout the pulp, and it will be apparent that the time and reagent concentration may be varied within wide ranges depending upon factors such as speed of operation and desired degree of phosphorylation. For example, to obtain 6% or better phosphorylation, a pickup of approximately 200% to 300% of the above reagent solution should be achieved. It is preferred to maintain the treating bath at a somewhat elevated temperature, for example, 60° C. to 70° C. to facilitate the penetration of the pulp boards.

After immersion, the pulp is cured at a temperature within the range of from about 125° C. to about 195° C. and preferably 180° C. to 190° C. Since the purpose of heating is to make energy available for the phosphorylation reaction, the amount of time required for this step depends upon the form and intensity of the applied energy as well as the quantity of pulp and the concentration of reagent therein. For example, the curing of wood pulp in an oven at 180° C. is preferably terminated when the pulp has turned light brown in color. On the other hand, the curing may be greatly accelerated by the use of a microwave over in which case the temperature of the pulp provides an indication of its cure state, and the curing is terminated when the temperature of the pulp rises after having first maintained a generally constant level. The use of microwaves also generally results in somewhat softer webs with very little of the discoloration which results from standard oven curing and is preferred for these reasons as well as reduced cure time.

After curing, the phosphorylated pulp is washed to remove excess reagents. It is then hydrolyzed with a dilute acid, preferably hydrochloric acid (2% to 5% by weight, for example). In some cases, depending upon the pulp used, hard fiber clumps may be present, and mild agitation may be used to break or soften them. Hydrolysis at a temperature of about 50° C. to 90° C. and preferably 60° C. to 70° C. for one-half hour to two hours is usually sufficient, after with the phosphorylated pulp is washed again with water.

Ther resulting hydrolyzed phosphorylated pulp is in its acid form and next is converted to its salt form by contact with an excess of base, for example, sodium carbonate (3 to 6% by weight). Preferably this contact takes place under conditions of agitation for at least about 15 minutes at room temperature. After washing to remove excess base, the phosphorylated pulp is in its preferred chemically modified form.

With phosphorylated pulp or other types of chemically modified cellulose, when it is desired to produce a web with high wicking rates, containment capacity, or the ability to absorb and retain large quantities of liquid, the next step is preferably refining of the chemically modified pulp. While it is not desired that the invention be limited to any particular theory, it is believed that the refining breaks away the outer shell, or primary wall of the fiber thus allowing it to expand and absorb more liquid.

When refining has been completed, the individual fibers, while retaining their individual identities, are in a highly swollen, gel-like form having a concentration preferably in the range of from 5% to 20%. At this point, particularly when physiological effects are to be considered, the pH of the fibers is adjusted to within the range of from about 4 to 9 and preferably 5.5 to 8 by the addition of dilute acid or base as needed. It will be recognized that this step may be carried out at a different time in the overall process or omitted entirely when dermatological factors need not be considered.

As thus produced, the phosphorylated pulp mixture extrudate is sometimes referred to hereinafter as "standard phosphorylated extrudate".

The dewatering step is important since it is preferred that most of the external water be removed so that only ±5 g/g of fiber of the fiber saturation point remains prior to spraying the mixture. It will be recognized that the actual consistency of the mixture with unbound water removed will vary with the type of chemical fiber modification and the prior processing history of the pulp.

Figure 27:
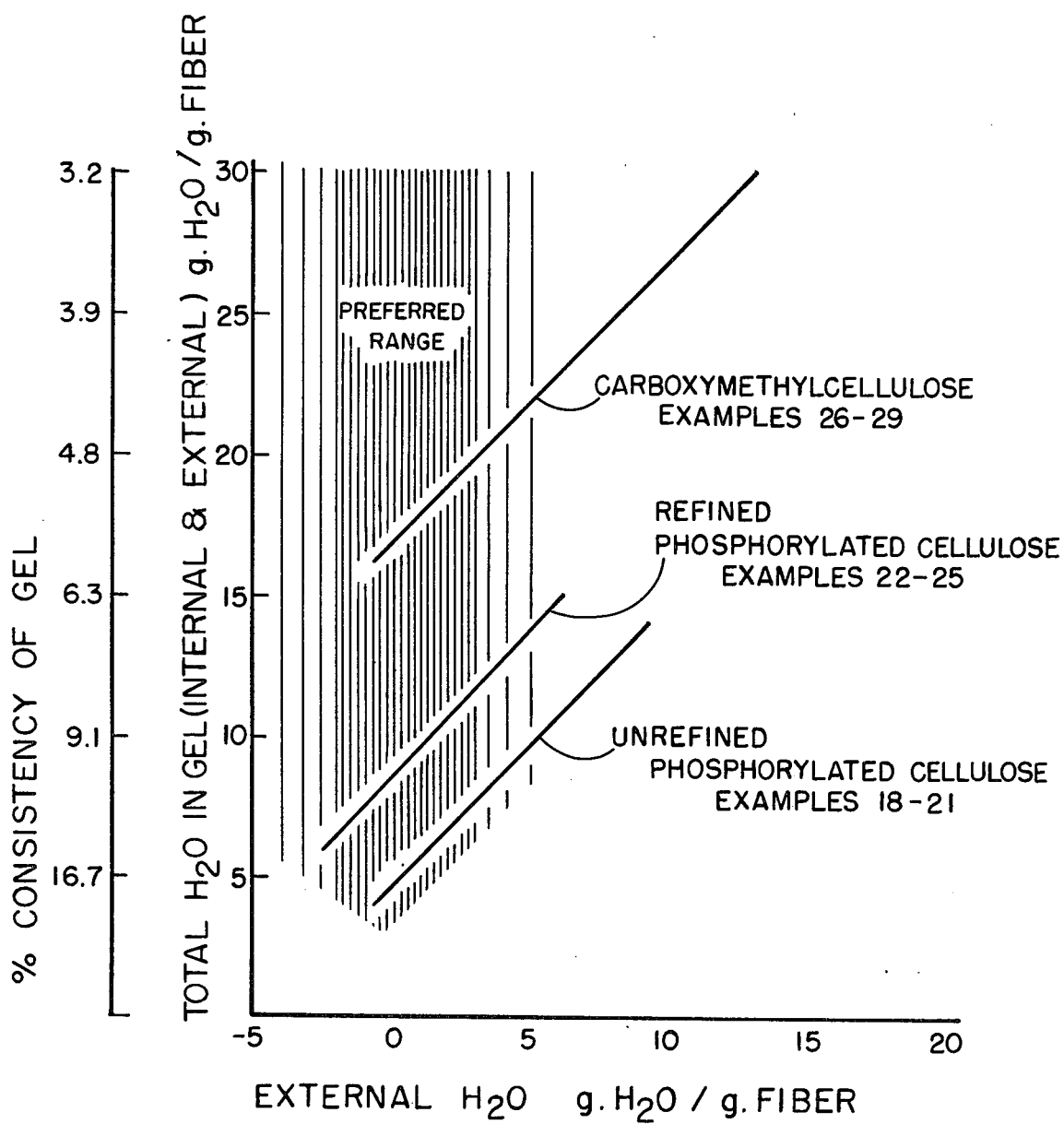
FIG. 27 illustrates consistency ranges as compared with preferred external water contents.

In all cases, however, as shown in FIG. 27, it is important that dewatering take place to the extent that external water remaining is within a range ±5 grams per gram of fiber and preferably ±3 grams per gram of fiber of the fiber saturation point as discussed in greater detail below and that the total water remaining be at least 4 grams per gram of fiber and preferably within a range ±3 grams per gram of fiber of the fiber saturation point. External water is defined as that which is removable by centrifuging for 30 minutes at an acceleration of 1000 times normal gravitational acceleration. Thus, the extrudates of the present invention do not embrace slurries or other compositions containing substantial amounts of free water such as are used in conventional papermaking techniques.

Figure 2:
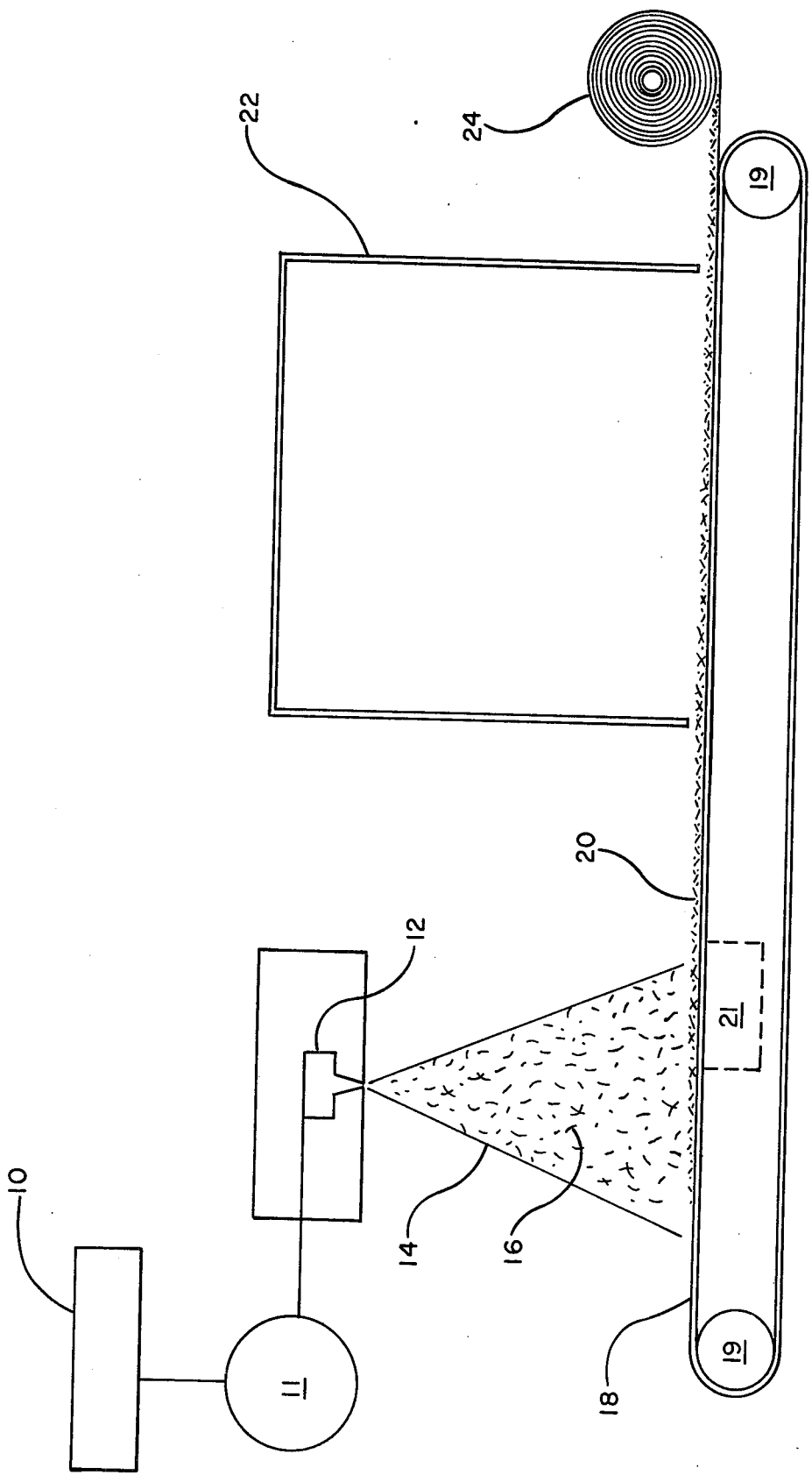
FIGS. 2–5 illustrate in schematic form and varying detail process embodiments of the present invention.

Turning also now to FIG. 2, it can be seen that the extrudate 10 is injected by pump 11 through spray nozzle 12 in the forming section which facilitates the separation of the extrudate into individual fibers 16. A stream 14 of separated, air-borne fibers 16 is sprayed directly onto a collecting surface 18 which may be an endless belt driven about rolls 19. The direction, temperature, and velocity of air stream 14 and carrier 18 are controlled to achieve a desired degree of fiber separation, placement and drying so that an undesirable amount of hydrogen bonding is avoided. Preferably the air stream is heated to a temperature in the range of from about 30° C. to about 160° C. for improved drying. Alternatively, nozzle 12 can be of the airless spray type. Fibers 16 are collected by means of carrier 18 as formed web 20. Vacuum box 21 may be used, if desired, to aid in web formation and increase the rate of fiber drying. This web 20 may be further dried if desired by dryer 22 and is illustrated as wound into rolls 24. Of course, it will be recognized that the resulting web from the process of the invention may be fed directly into apparatus for the manufacture of end use products such as sanitary napkins, disposable diapers, and the like.

Figure 3:
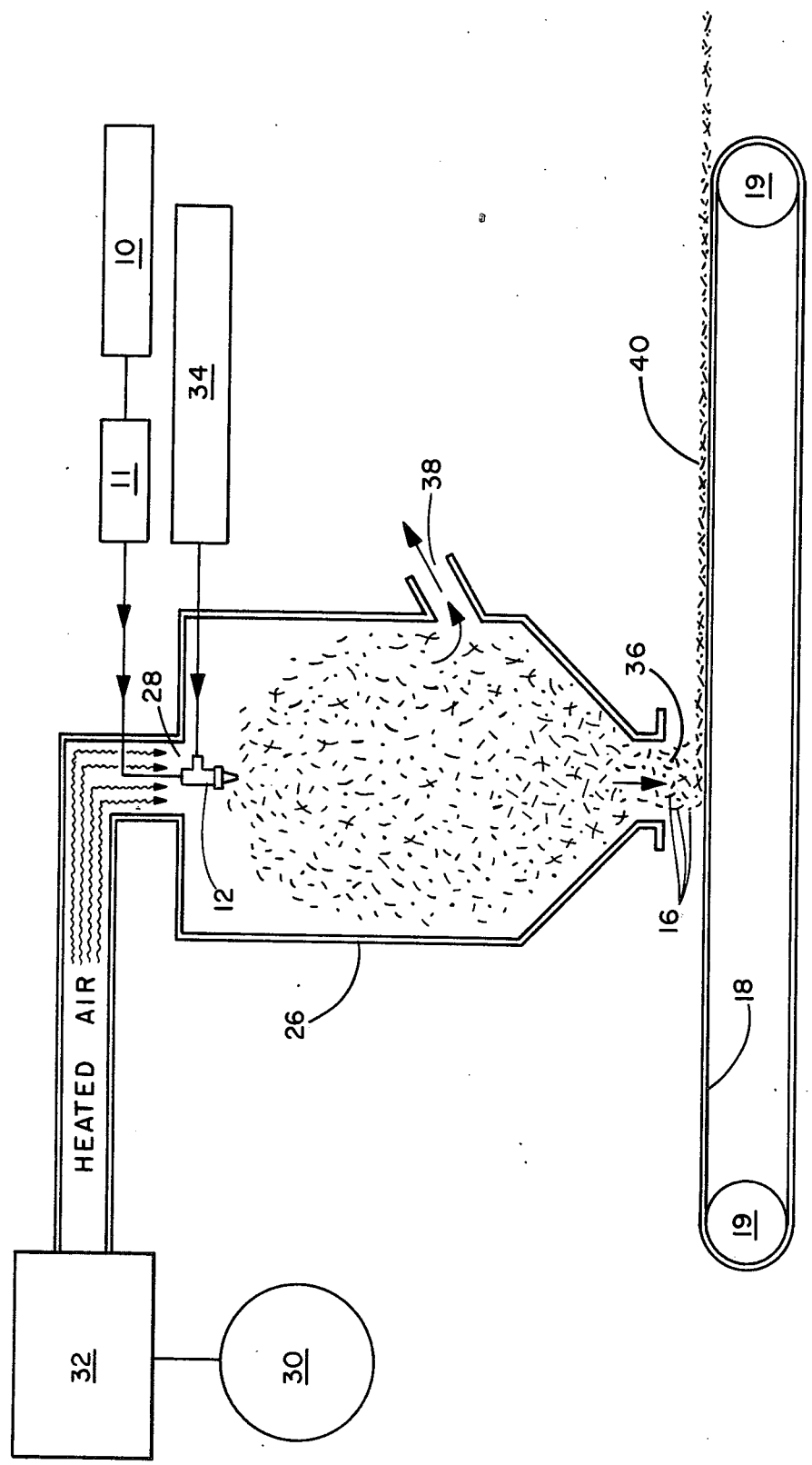
Figure 6:
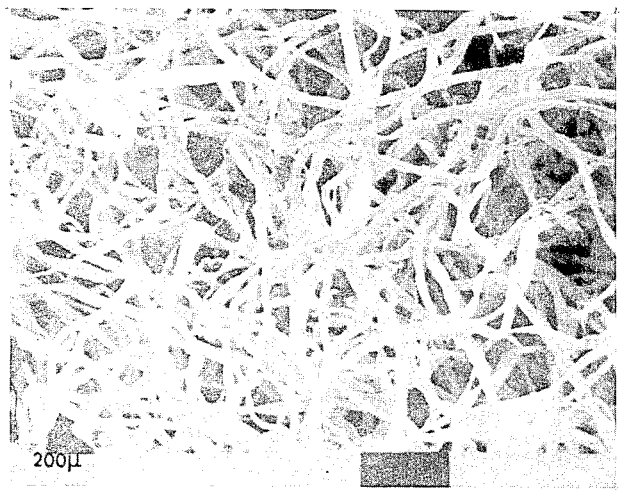
FIGS. 6–25 are magnified photographic representations of various views of webs formed in accordance with the invention are webs illustrating unsatisfactory results.
Figure 7:
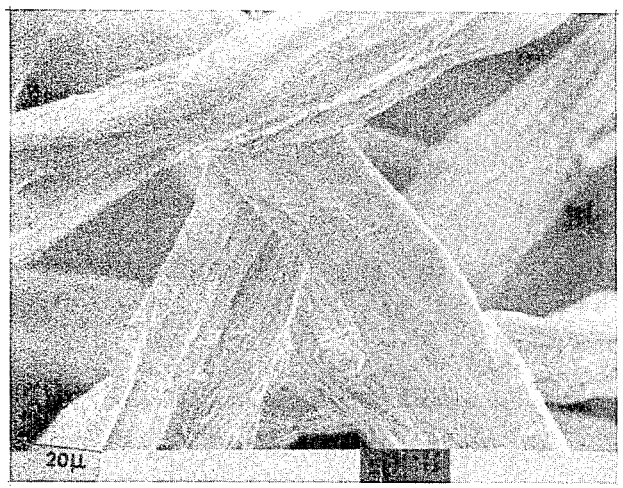

In FIG. 3 a web forming embodiment is illustrated in greater detail. Drying chamber 26 includes inlet 28 for heated air provided by blower 30 and heater 32. Also within drying chamber 26 is spray nozzle 12 fed with extrudate 10 by pump 11 and compressed air by line 34. Dried fibers 16 exit at opening 36 with exhaust air vented at 38. The random deposition of fibers on carrier 18 forms a fluff batt 40 which may be further dried, if desired, and processed as shown in FIG. 2. The drying chamber 26 allows the fibers 16 to be substantially dried prior to deposition so that they are lighter and produce a thick, fluffy, airy mat with a high degree of z-direction fiber orientation. Such a web formed from phosphorylated pulp fibers is shown in FIGS. 6 and 7 at magnifications of 100× and 1000×, respectively. The lack of interfiber bonding and large void areas resulting from predrying are apparent.

Figure 4:
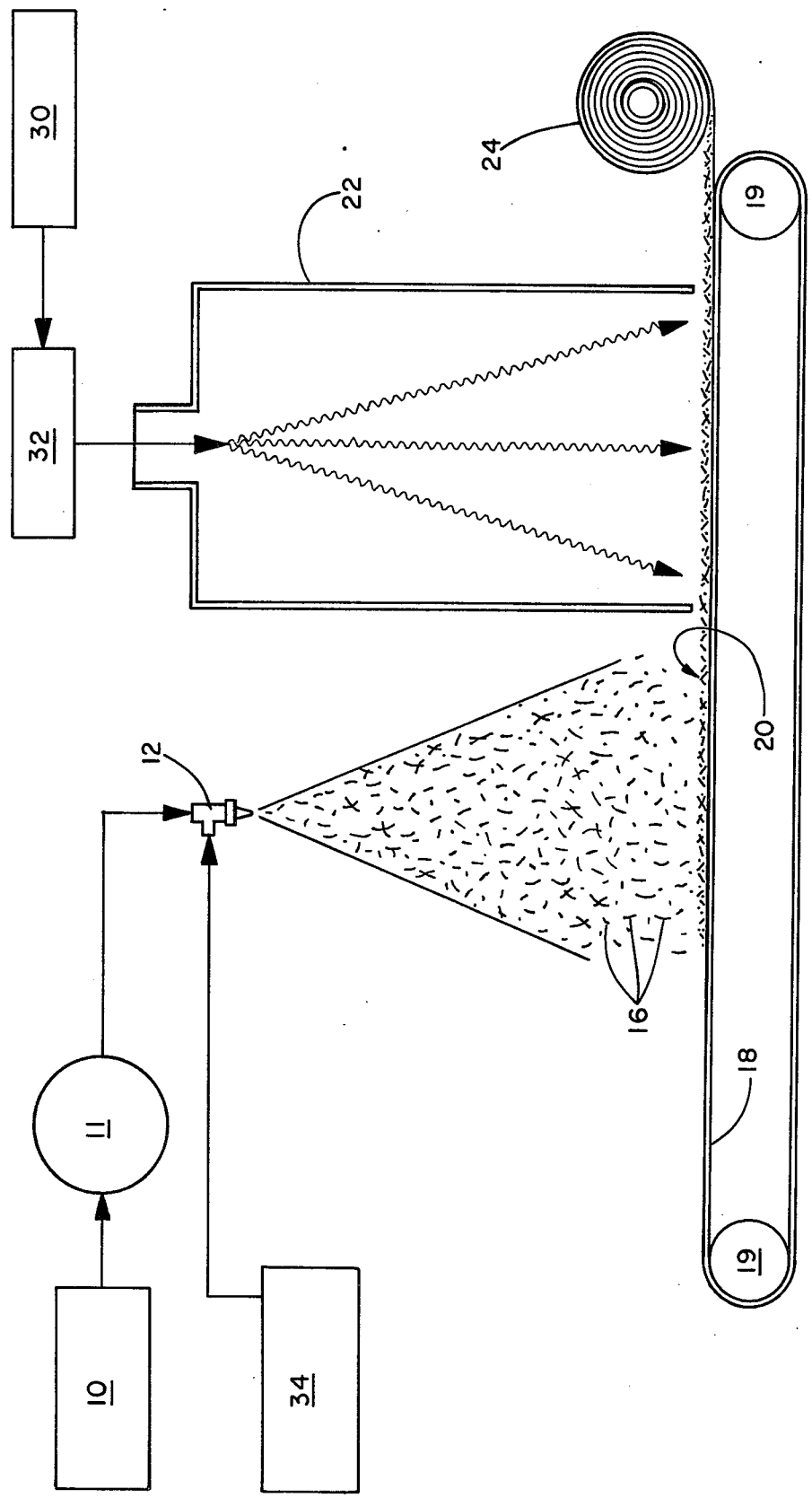
Figure 8:
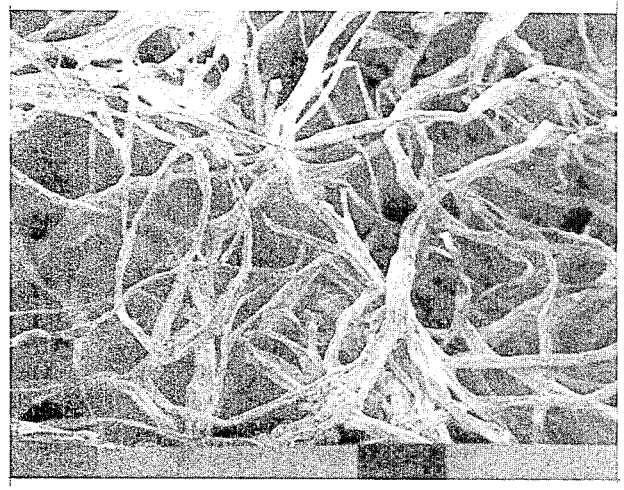
Figure 9:
Figure 10:
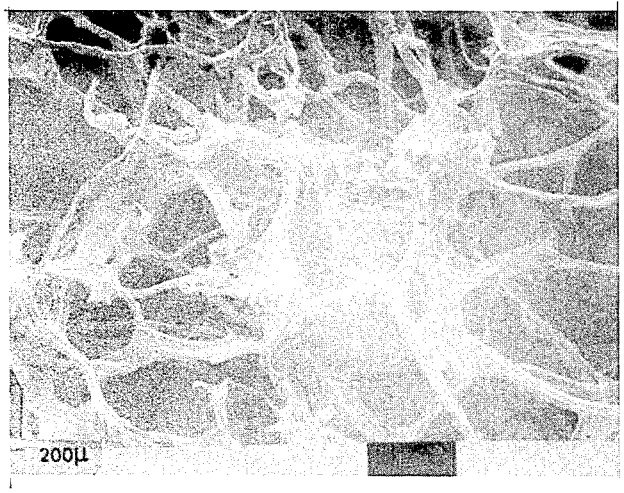
Figure 11:
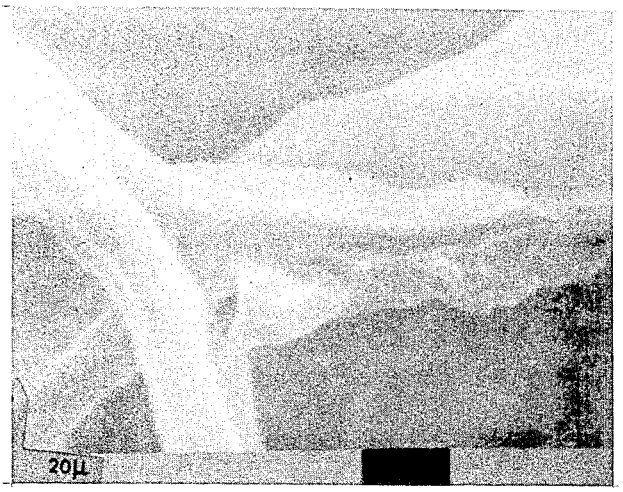

FIG. 4 illustrates an embodiment wherein the process of FIG. 2 is modified by adding compressed air to spray nozzle 12 and means for heating the air in dryer 22. The fibers 16 are wet as web 20 is formed and the web is dried as it passes through dryer 22. The result is a somewhat more highly bonded, thin mat as shown in the photomicrographs of FIGS. 8 and 9 shown at magnifications of 100× and 1000×, respectively. FIGS. 10 and 11 similarly illustrate the results obtained with Buckeye brand carboxymethyl cellulose fibers.

Figure 5:
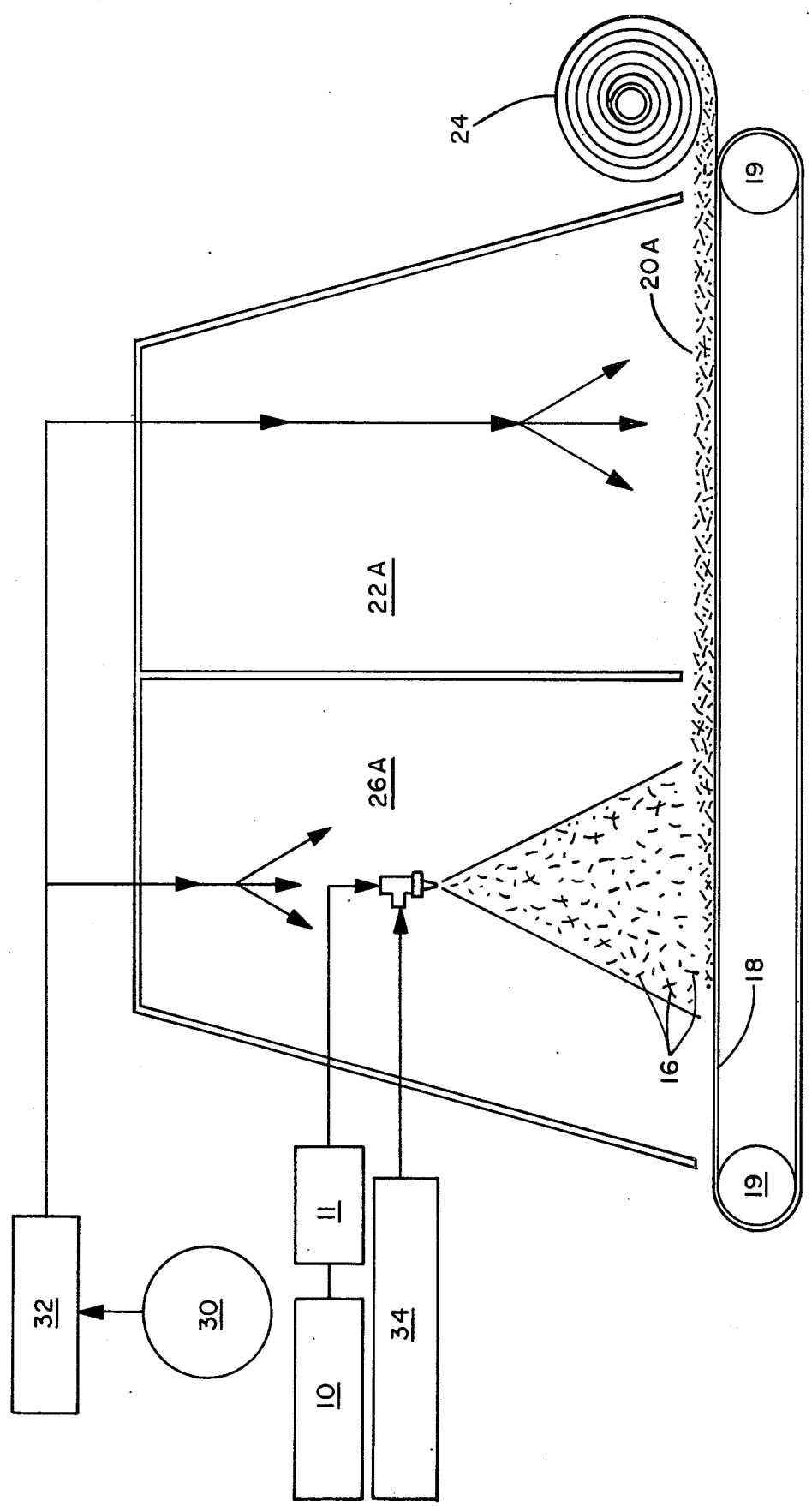

FIG. 5 illustrates still a third web forming embodiment wherein partial drying is first obtained in primary drying chamber 26A and final drying is accomplished in secondary drying chamber 22A. Both dryers are supplied with heated air for more rapid drying.

Figure 12:
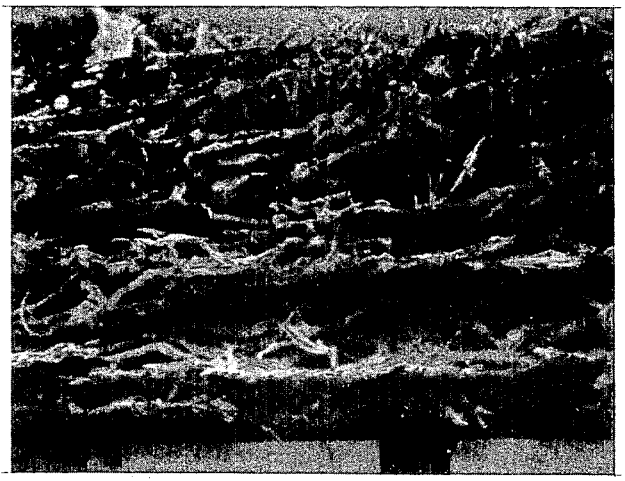

FIG. 12 is a microphotograph cross-section of the web of FIGS. 7 and 8 taken at a magnification of 50× illustrating the layered structure obtainable with this embodiment of the invention.

The invention will now be further described by way of specific examples.

EXAMPLE 1

A standard phosphorylated extrudate at 6.5% dry fiber consistency was extruded from a 20 milliliter disposable syringe acting as pump and reservoir using appropriate fittings into the liquid port of a pneumatic spray nozzle fitted for 30 psi compressed air. The pneumatic spray nozzle was equipped with a slotted dispersing tip and 5 milliliters of extrudate were manually injected through the pneumatic sprayer (Spraying Systems Company Model ¼ J fitted with dispersing tip No. 125328 SS over dispersing head No. 2050 with a liquid port opening of 0.50 inch) to suspend the fibers individually. The compressed air was fed into the air port at room temperature. This fiber suspension was collected in a uniform layer of separated fibers on a 12 inch×12 inch×⅛ inch sheet of Teflon brand fluorinated ethylene-propylene resin, and these separated fibers were subsequently air dried five minutes using the high velocity air from the spray nozzle. The result was a fluff-like collection of fibers having a dry fiber consistency of 85.2%.

EXAMPLE 2

Example 1 was repeated except that the fiber collection was dried for 2 minutes with air at a temperature of 85° C. from a Master Appliance laboratory hot air heat gun (Model No HG301J). The resulting fluff-like collection of fibers had a dry fiber consistency of 86.5%.

EXAMPLE 3

The extrudate of Example 1 was spread by the use of a doctor blade system in a thin film approximately 0.1 inch thick and gradually dried for 18 hours at a temperature of 105° C. in a circulating Blue "M" oven. The resulting sheet was harsh, crust-like, and slowly rewettable being partially swollen under microscopic observation when wet.

EXAMPLE 4

A standard phosphorylated extrudate was suspended in a slurry of acetone and solvent dried in the manner described in the above-referenced Bernardin patent. The resulting mat of solvent dried fibers was soft, flexible, rapidly rewettable and highly swollen under microscopic observation when wet.

EXAMPLE 5

A crosslinked carboxymethyl cellulose extrudate having 3.0% dry fiber consistency was prepared by mixing 1.0 gram of dry fluff Buckeye Cellulose Company (CLD SR-447) fibers in 32.3 grams of distilled water. This extrudate was formed into a web using a pneumatic spray nozzle and dried as in Example 1. The resulting collection of fibers was soft, fluff-like, very slowly rewettable and extremely swollen under microscopic observation when wet. The dry fiber consistency of the resulting web was 81.3%.

EXAMPLE 6

Example 2 was repeated using the carboxymethyl cellulose extrudate of Example 5. The resulting collection of fibers was soft, fluff-like, very slowly rewettable and extremely swollen under microscopic observation when wet. The mat had a dry fiber consistency of 82.7%.

EXAMPLE 7

Example 3 was repeated using the carboxymethyl cellulose extrudate of Example 5. The resulting sheet was harsh and crust-like, extremely slow to rewet but eventually highly swollen under microscopic observation when wet.

EXAMPLE 8

A sample of crosslinked carboxymethyl cellulose from Buckeye Cellulose Company (SR44) as received from the supplier, previously solvent dried. This soft fluff was very slowly wettable and extremely swollen under microscopic observation when wet.

The following Table 1 summarizes the foregoing Examples and the results of 1000 G retention tests performed with water and saline solutions.

Table 1

| Example | Pulp | Drying Method | 1000 G Retention (grams/gram) | |
|---|---|---|---|---|
| | | | Water | Saline |
| 1 | Phosphorylated | Present invention High velocity air | 10.49 | 3.49 |
| 2 | Phosphorylated | Present invention Heated air | 8.27 | 3.17 |
| 3 | Phosphorylated | Air drying of thick film of extrudate | 3.51 | 2.16 |
| 4 | Phosphorylated | Acetone drying of fibrous mat | 8.77 | 3.52 |
| 5 | CMC | Present invention High velocity air | 49.76 | 20.83 |
| 6 | " | Present invention Heated air | 35.90 | 15.72 |
| 7 | " | Air drying of thick film of extrudate | 21.47 | 13.53 |
| 8 | " | As received from supplier | 67.97 | 18.72 |

As the foregoing Examples demonstrate, materials produced according to the invention (Examples 1, 2, 5 and 6) exhibit absorbent characteristics essentially equal to those of the same fibers dried according to solvent-drying techniques and far superior to those air dried in a thick film (Examples 3 and 7). They further demonstrate that in accordance with the invention highly absorbent fibers can be individually suspended through the use of pneumatic sprayers, air sprayers, centrifugal sprayers, and the like. Thus, highly absorbent fibers in a desirable soft, flexible mat form can be prepared without requiring solvent-drying techniques, producing significant savings in cost and handling over traditional drying routes. The results for Example 8, while showing high absorbency are for a fluff form, not a web.

The following Examples demonstrate, through alternative embodiments, the variety of results obtainable in accordance with the present invention.

EXAMPLE 9

A standard phosphorylated extrudate at 6.5% dry fiber consistency was extruded from a 20 milliliter syringe through a 16 gauge (I.D.=0.046 inch) needle and into an air line supplying air at room temperature and pressure at 15 psi. The sprayer was hand operated at about 1 foot above a collecting surface and the individual suspended fibers were directed into a separate air stream at a temperature of 85° C. from a distance of about 1 foot to the collecting surface. The partially dried fibers were collected on a sheet of 0.25 oz/yd$^2$ spunbonded polypropylene available under the trademark EVOLUTION which was placed over a vacuum box with laboratory vacuum applied. The web was substantially dried as collected to form an airy, mat-like structure. Sixty milliliters of extrudate were sprayed and dried over a 15 minute interval. This structure had a dry fiber consistency of 83.2% and the following characteristics:

Thickness—0.56 centimeters,
Bulk density—0.031 gram/cubic centimeter,
Free standing saline absorbency—33.1 grams liquid/gram fiber,
1000 G water retention—3.93 grams liquid/gram fiber,
1000 G saline retention—3.00 grams liquid/gram fiber,
Wicking time—0.12 minutes,
As is tensile—830 grams/centimeter,
As is breaking length—474 meters, Wet Tensile—43 grams/centimeter, and
Wet breaking length—25 meters.

EXAMPLE 10

Example 9 was repeated except that only 20 milliliters of extrudate were sprayed and dried over a 5 minute interval. This structure had a dry fiber consistency of 83.7% and the following characteristics:
Thickness—0.13 centimeters,
Bulk density—0.047 gram/cubic centimeter,
Free standing saline absorbency—43.6 grams liquid/gram fiber
1000 G water retention—6.82 grams/liquid/gram fiber,
1000 G saline retention—2.92 grams liquid/gram fiber,
Wicking time—0.35 minute,
As is tensile—150 grams/centimeter,
As is breaking length—246 meters,
Wet tensile—4 grams/centimeter, and
Wet breaking length—6 meters.

EXAMPLE 11

Example 9 was repeated except that the collecting surface was EVOLUTION spunbonded polypropylene placed on a flat solid surface, and the fibers were directed at an upward 45° angle to allow the individually suspended fibers to arch upward and then fall softly downward (a distance of approximately 3 feet) to the collecting surface. Two laboratory heat guns were positioned to blow air at a temperature of 85° C. across this collecting surface. Approximately 200 milliliters of extrudate were sprayed and dried over a 30 minute interval. The resulting structure had a dry fiber consistency of 87.9% and the following characteristics:
Thickness—0.22 centimeters,
Bulk density—0.11 gram/cubic centimeters,
Free standing saline absorbency—28.9 grams liquid/gram fiber,
1000 G water retention—6.41 grams liquid/gram fiber
1000 G saline retention—2.51 grams liquid/gram fiber,
Wicking time—very slow,
As is tensile—96 grams/centimeter,
As is breaking length—384 meters,
Wet tensile—not measurable, and
Wet breaking length—not measurable.

EXAMPLE 12

Example 11 was repeated except that the collecting surface was a 12 inch × 12 inch copper collecting wire (200 mesh) and the fibers were allowed to fall softly in their wet state. This structure was placed in a Blue "M" oven set at 105° C. and dried for five minutes. The resulting structure had a dry fiber consistency of 82.5% and the following characteristics:
Thickness—0.18 centimeters,
Bulk density—0.012 gram/cubic centimeter,
Free standing saline absorbency—29.3 grams liquid/gram fiber,
1000 G water retention—6.47 grams liquid/gram fiber,
1000 G saline retention—2.16 grams liquid/grams fiber,
Wicking time—very slow,
As is tensile—59 grams/centimeter,
As is breaking length—281 meters,
Wet tensile and wet breaking length not measurable.

EXAMPLE 13

A sample of web was prepared according to the procedure described in the above-mentioned Lassen patent using the extrudate described in Example 4. The resulting web had a dry fiber consistency of 85% and the following characteristics:
Thickness—0.48 centimeters,
Bulk density—0.033 gram/cubic centimeters,
Free standing saline absorbency—20.5 grams/gram,
1000 G water retention—7.86 grams liquid/gram fiber,
1000 G saline retention—3.69 grams liquid/gram fiber,
Wicking time—0.90 minutes,
As is tensile (M.D.)—70 grams/centimeter,
As is breaking length (M.D.)—43 meters,
Wet tensile and wet breaking length not measurable.

As can be seen, the present invention is exemplified by Examples 9, 10, 11 and 12 can be used to produce a web similar to solvent-dried material in thickness, bulk density, and saline wicking rate. More importantly, it can also be seen that the materials formed by this invention possess a greater free standing saline absorbency (33.1 grams/gram as compared to only 20.5 grams/gram of solvent-dried material—Example 13) and superior web and dry tensile properties (830 grams/centimeter compared to only 70 grams/centimeter for the solvent-dried material plus a wet tensile of 43 grams/centimeter compared to the fact that this property was not measurable by standard techniques used on the Instron Tensile Tester with the solvent-dried material). Example 11 demonstrates a material having considerably lower bulk density and strength as well as showing the effect of velocity of the sprayed fibers on the type of structure which is formed on the collecting surface. This material has similar physical characteristics to that of the material produced by Example 12. In Example 11, the fibers were partially dried as sprayed and subsequently dried as collected on the collecting surface. In Example 12 a still lesser degree of initial drying was obtained since the fibers were sprayed wet without an auxiliary drying air stream as in Example 11. The result was a wet, open structure with a thickness of approximately ⅜ inch. This web was placed in a circulating oven to dry. These examples of the present invention show similar characteristics to airformed paper products but with surprising strength and absorbency.

EXAMPLE 14

Phosphorylated pulp as in Example 1 was pumped at a pressure of 300 psig by means of a Zenith Model BPB4391 pump through a TEJET tip No. SS6501 to form an airless spray onto black blotting paper under ambient conditions. A somewhat flaky web was formed. Under higher pressures a more uniform web would be expected.

In a further embodiment the present invention may provide an improved material combining chemically modified fibers with other highly absorbent materials. For example, acrylonitrile grafted starch granules have been available but present difficulties in handling and incorporation into absorbent products due to dusting, sifting and positioning problems related to the free flowing nature of such materials. By combining these granular or powder materials having a mesh size from about 14 to 400, for example, with chemically modified fibers prior to complete drying an integrated composite material is formed that can be handled and reduces dusting problems. The following examples demonstrate this embodiment.

EXAMPLE 15

Phosphorylated pulp having 7.2% phosphorous and a consistency of 10.5% fibers was sprayed from a pressurized reservoir to a Zenith laboratory metering unit (Model 175G) equipped with a type BPB (1.7 cc/revolution) spinning pump through a high pressure hose to a Spraying Systems Company ¼ J pneumatic nozzle fitted with a 60100 fluid cap and 125328 air cap. The nozzle was mounted 18 inches above a forming wire with the flat spray air cap aligned in the cross direction and the nozzle tilted at an angle of about 60° from vertical. The gel was pumped into the nozzle and pneumatically sprayed. From a Syntron vibrator pan General Mills polymer 502S granules were allowed to free fall about 15 inches into the fiber spray and the composite material collected on a forming wire. After through drying at 30° C., a sheet of 5% phosphorylated fibers and 95% granules by weight was formed having high tensile strength (361 g/cm), 1000 G saline retention of 25.4 g/g, density 0.15 g/cc, and a thickness of 0.25 cm.

Example 16

Phosphorylated pulp (8.3% phosphorous) gel having a consistency of 10.2% solids was sprayed as in Example 15, and Grain Processing polymer 35-A-100 was sifted from a separatory funnel into the spray at the outlet of the spray cap. After collecting on a fourdrinier wire and through drying at 70° C. a composite containing 10% phosphorylated fibers and 90% polymer was formed having a tensile strength of 35 g/cm, 1000 G saline retention of 12.1 g/g, density of 0.08 g/cc and thickness of 0.22 cm.

EXAMPLE 17

Carboxymethyl cellulose (Hercules Aqualon "R") fiber gel was mixed with water to 1% consistency and dewatered to 7.8% consistency. It was sprayed as in Example 15 and mixed at the spray nozzle with General Mills polymer 502S added with a Vibra Screw feeder (Model SCR-20). The composite was through dried at 30° C. and resulted in a web containing 17% fibers and 83% granules having a tensile of 220 g/cm, a 1000 G saline retention value of 28.5 g/g, density of 0.09 g/cc and a thickness of 0.19 cm.

EXAMPLE 18

Figure 13:
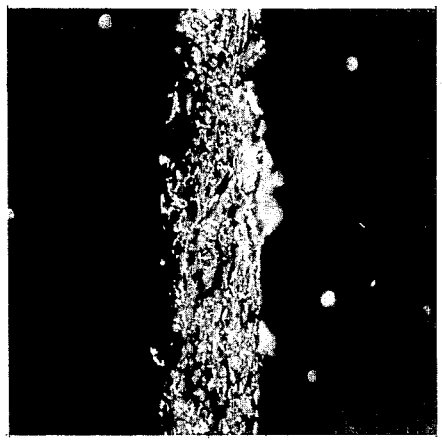

Unrefined 700 Canadian Standard Freeness phosphorylated pulp gel having a 7.0% phosphorous, and a consistency of 6.7% solids (fiber saturation point 4.5 g/g, total water content 14 g/g) was pumped from a pressurized reservoir to a Zenith Laboratory metering unit Type 1-QF equipped with a type BPB (1.7 cc/revolution) spinning pump and then through a high pressure hose to a Spraying Systems Company ¼ J pneumatic nozzle fitted with a 100150 fluid cap and a 189 351 air cap. The nozzle was mounted 40 inches above a centerline from a 19 inch wide forming wire with the pneumatic nozzle flat spray air cap aligned in the cross direction and nozzle aligned so that the fibers were sprayed directly downward toward the forming wire which was traveling at 8 inches/minute. Sufficient compressed air was used to just separate the gel into fibers with minimum excess air. The Zenith pumping unit was set at 35 (equivalent to 250 RPM's). Approximately 4 lineal feet of undried web was produced. This was then run through a 4 foot long tunnel type through dryer approximately 10 feet from the spray nozzle. The through dryer was set at 100° C. The web was very difficult to dry, but after 25 minutes of visual inspection it was dry. The resulting web, as shown in FIG. 13, magnified 12×, was crusty and not acceptable for most applications.

EXAMPLE 19

Figure 14:
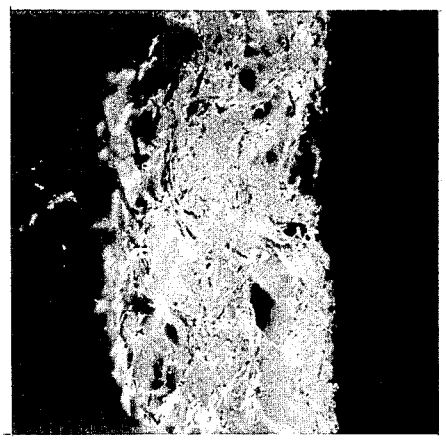

Example 18 was repeated except that the pulp gel was at 8.7% consistency (total water 10.5 g/g); 12 psi was used to pneumatically separate the gel fibers, and the web was through dried in 11 minutes. A poor quality web resulted as shown in FIG. 14, magnified 12×.

EXAMPLE 20

Figure 15:
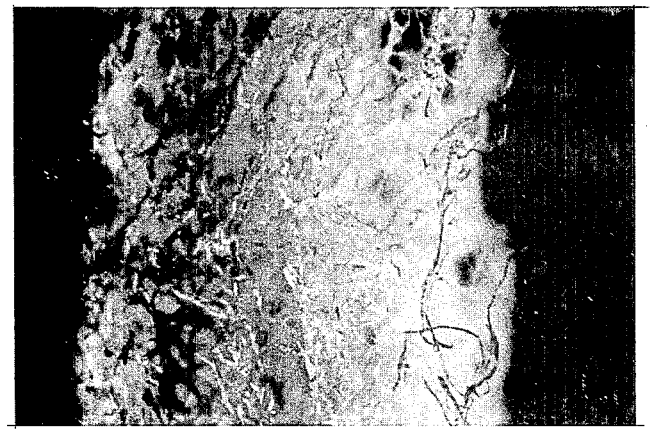

Example 18 was repeated except that the pulp gel was at 13.0% consistency (total water 6.7 g/g); 30 psi was used to pneumatically separate the gel fibers and the web was through dried in 6 minutes. A good quality web resulted as shown in FIG. 15, at 12×.

EXAMPLE 21

Figure 16:
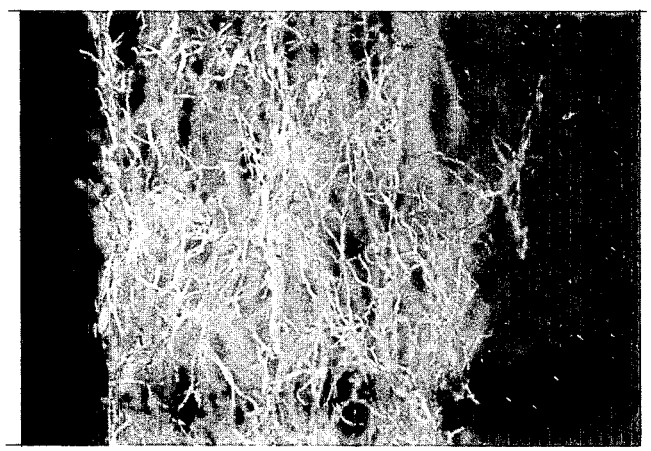

Example 18 was repeated except that the pulp gel was at 18.4% consistency (total water: 4.4 g/g); 65 psi was used to pneumatically separate the gel fibers, and the web was through dried in 1 minute. An excellent quality web, foam-like in appearance, resulted as shown in FIG. 16, at 12×.

EXAMPLE 22

Figure 17:
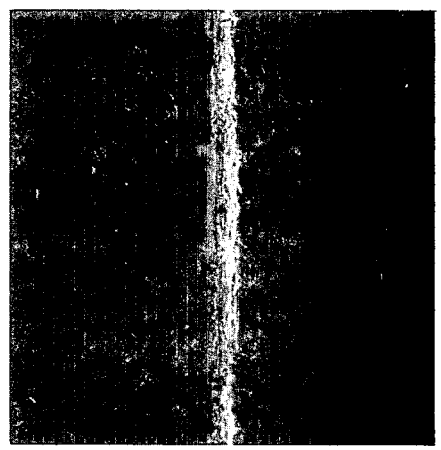

Example 18 was repeated except that the pulp gel was refined to 400 Canadian Standard Freeness. This was sprayed at 6.7% consistency (total water: 14 g/g, fiber saturation point: 8.5 g/g) 5 psi was used to pneumatically separate the gel fibers and the web was through dried in 21 minutes. The web quality was very poor and crust-like in appearance as shown in FIG. 17, magnified 12×.

EXAMPLE 23

Figure 18:

Example 22 was repeated except that the pulp gel was at 8.7% consistency (total water: 10.5 g/g); 15 psi was used to pneumatically separate the gel fibers and the web was through dried in 10 minutes. Although the external water content was within the preferred range, a somewhat crusty web resulted as shown in FIG. 18, magnified 12×, possibly due to the high degree of refining.

EXAMPLE 24

Figure 19:
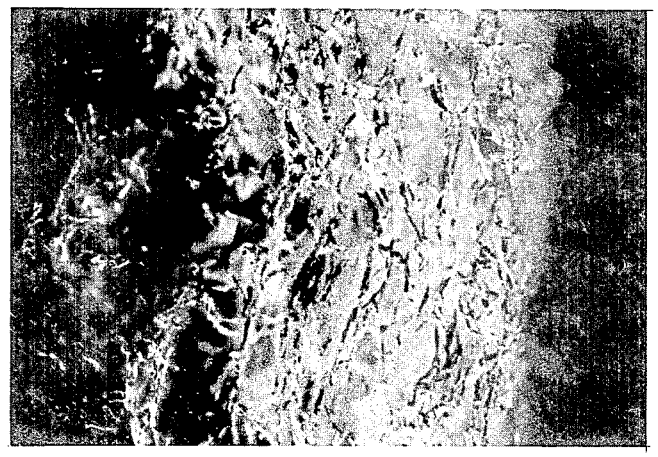

Example 22 was repeated except that the pulp gel was at 10.0% consistency (total water: 9.0 g/g); 43 psi was used to pneumatically separate the gel fibers and the web was through dried in 6 minutes. A good quality web resulted as shown in FIG. 19, magnified 12×.

EXAMPLE 25

Figure 20:

Example 22 was repeated, except that the pulp gel was at 13.0% consistency (total water: 6.7 g/g, dewatered by vacuum); 32 psi was used to pneumatically separate the gel fibers and the web was through dried in 6 minutes. A good web, foam-like in appearance, was obtained as shown in FIG. 20, magnified 12×.

EXAMPLE 26

Figure 21:

Example 18 was repeated except that the pulp gel was carboxymethyl cellulose (Hercules Aqualon "R"). It was sprayed at 3.2% consistency (total water: 30 g/g, fiber saturation point: 16.5 g/g); 23 psi was used to pneumatically separate the gel fibers; the forming wire was run at 4 inches per minute; and the web was through dried in 25 minutes. A poor web, very boardlike, was obtained as shown in FIG. 21, magnified 12×.

EXAMPLE 27

Figure 22:
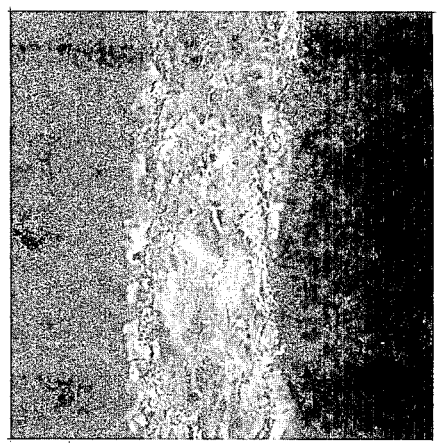

Example 26 as repeated except that the pulp gel was at 4.0% consistency (total water: 24.0 g/g); 35 psi was used to pneumatically separate the gel fibers; the forming wire was at 8 inches/minute and the web was through dried in 6 minutes. A poor web resulted as shown in FIG. 22, at 12×.

EXAMPLE 28

Figure 23:
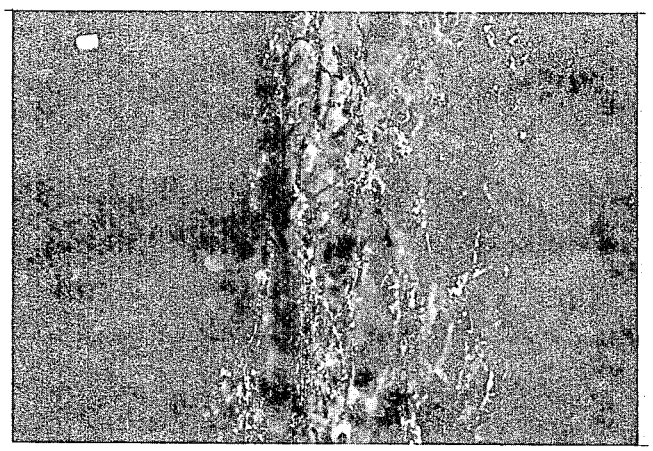

Example 26 was repeated except that the pulp gel was at 5.0% consistency (total water: 19.0 g/g); 12 psi was used to pneumatically separate the gel fibers; the forming wire was run at 3 inches per minute; and the web was through dried in 3 minutes. A good web resulted as shown in FIG. 23, at 12×.

EXAMPLE 29

Figure 24:
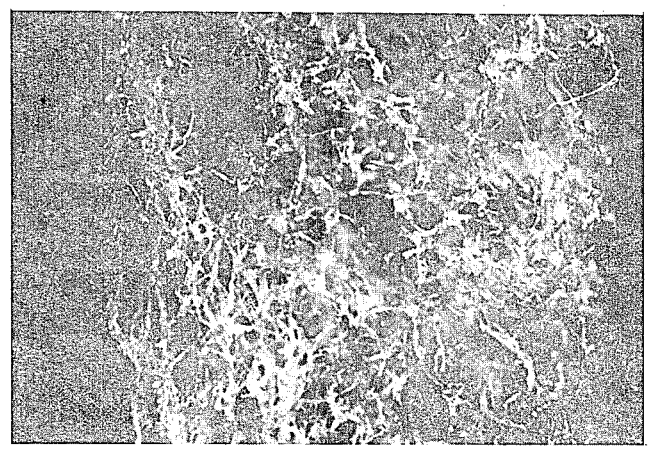

Example 26 was repeated except that the gel was at 5.8% consistency (total water: 16.4 g/g); 25 psi was used to pneumatically separate the gel fibers; the forming wire was run at 2 inches per minute and the web was through dried in 1 minute. A good web resulted as shown in FIG. 24, at 12×.

EXAMPLE 30

Figure 25:
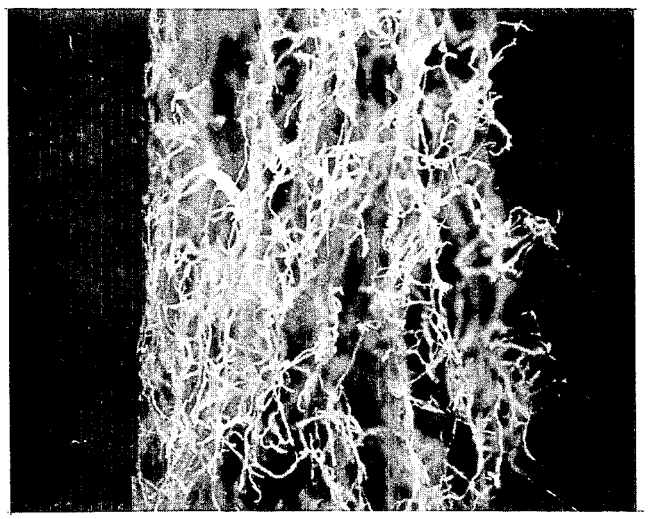

Example 22 was repeated except that 60 psi was used to pneumatically separate gel instead of 5 psi; the gel feed pump was set at 3 instead of 35; the forming wire was stopped due to reduced feed rate in order to allow sprayed fibers to build-up a reasonable basis weight so approximately 1 lineal foot of web was produced. The web was through dried in 1 minute. The web was very soft. Much drying occurred during formation due to the high ratio of air to gel during spraying which results in the material being formed at or near the fiber saturation point in spite of the high gel water content. Similar results are shown in e.g. Example 1. The web had a 17.1% consistency prior to through drying. FIG. 25 shows the web of this Example, magnified 12×.

Figure 28:
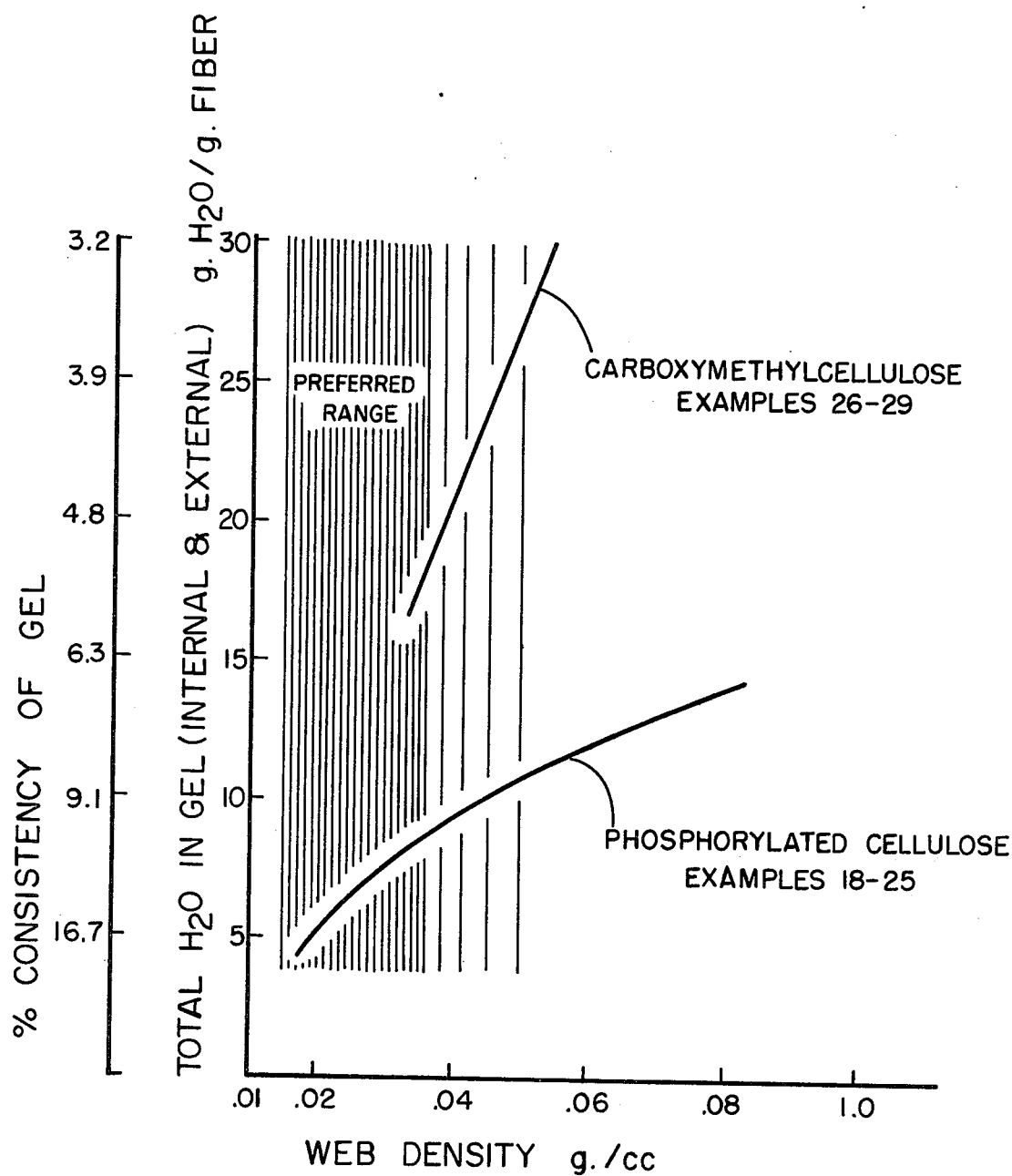
FIG. 28 illustrates consistency ranges as compared with preferred web densities.

The results of these Examples are further illustrated in Table 2. As shown, good (soft, noncrusty) webs can be produced by selecting a combination of consistency, flow and drying conditions to achieve maximum fiber separation requiring a minimum of subsequent drying. As shown in FIG. 28, preferred web densities after drying are in the range of about 0.015 to 0.050 grams/cc with the range of about 0.015 to 0.040 especially preferred.

Table 2

| Ex. | Modified Cellulose Type | Fiber Saturation Point 900 "G" g/g | Base Gel Grams $H_2O$/Gram Fiber | Base Gel % Consistency | Spray Web Prior to Thru Drying % Consistency | Basis Weight $g/m^2$ | Density g/cc | Normalized Thickness Centimeters At A Basis Weight 200 $g/m^2$ | Normalized Tensile Kg/15 mm At A Basis Weight 200 $g/m^2$ | Stretch % | Thru Drying Time At 100° C. Minutes | Photo Reference |
|---|---|---|---|---|---|---|---|---|---|---|---|---|
| 18 | Phosphorylated Unrefined | 4.5 | 14.0 | 6.7 | 6.9 | 163 | .083 | .24 | 1.7 | .86 | 25 | 113 |
| 19 | Phosphorylated Unrefined | 4.5 | 10.5 | 8.7 | 9.1 | 182 | .047 | .43 | 1.9 | .87 | 11 | 14 |
| 20 | Phosphorylated Unrefined | 4.5 | 6.7 | 13.0 | — | 184 | .028 | .72 | 1.9 | 4.52 | 6 | 15 |
| 21 | Phosphorylated Unrefined | 4.5 | 4.4 | 18.4 | — | 85 | .016 | 1.28 | 1.1 | 8.05 | 1 | 16 |
| 22 | Phosphorylated Refined | 8.5 | 14.0 | 6.7 | 6.8 | 150 | .065 | .31 | 3.6 | .77 | 21 | 17 |
| 23 | Phosphorylated Refined | 8.5 | 10.5 | 8.7 | 9.2 | 127 | .058 | .34 | 3.1 | 2.64 | 10 | 18 |
| 24 | Phosphorylated Refined | 8.5 | 9.0 | 10.0 | — | 198 | .030 | .66 | 1.4 | 2.67 | 6 | 19 |
| 25 | Phosphorylated Refined | 8.5 | 6.7 | 13.0 | — | 177 | .033 | .59 | 1.4 | 2.77 | 6 | 20 |
| 26 | CMC Unrefined | 16.5 | 30.0 | 3.2 | 3.4 | 162 | .050 | .40 | 2.9 | 1.99 | 25 | 21 |
| 27 | CMC Unrefined | 16.5 | 24.0 | 4.0 | 4.2 | 113 | .051 | .39 | 2.4 | 2.82 | 8 | 22 |
| 28 | CMC Unrefined | 16.5 | 19.0 | 5.0 | 5.1 | 149 | .035 | .57 | 2.5 | 3.00 | 6 | 23 |
| 29 | CMC Unrefined | 16.5 | 16.4 | 5.8 | 6.1 | 182 | .034 | .59 | 1.5 | 3.72 | 3 | 24 |
| 30 | Phosphorylated Refined | 8.5 | 14.0 | 6.7 | 17.1 | 65 | .015 | 1.33 | 1.8 | 13.86 | 1 | 25 |

While it is not desired to limit the invention to any particular theory, the following is offered as a possible explanation of the results obtained.

Figure 26:
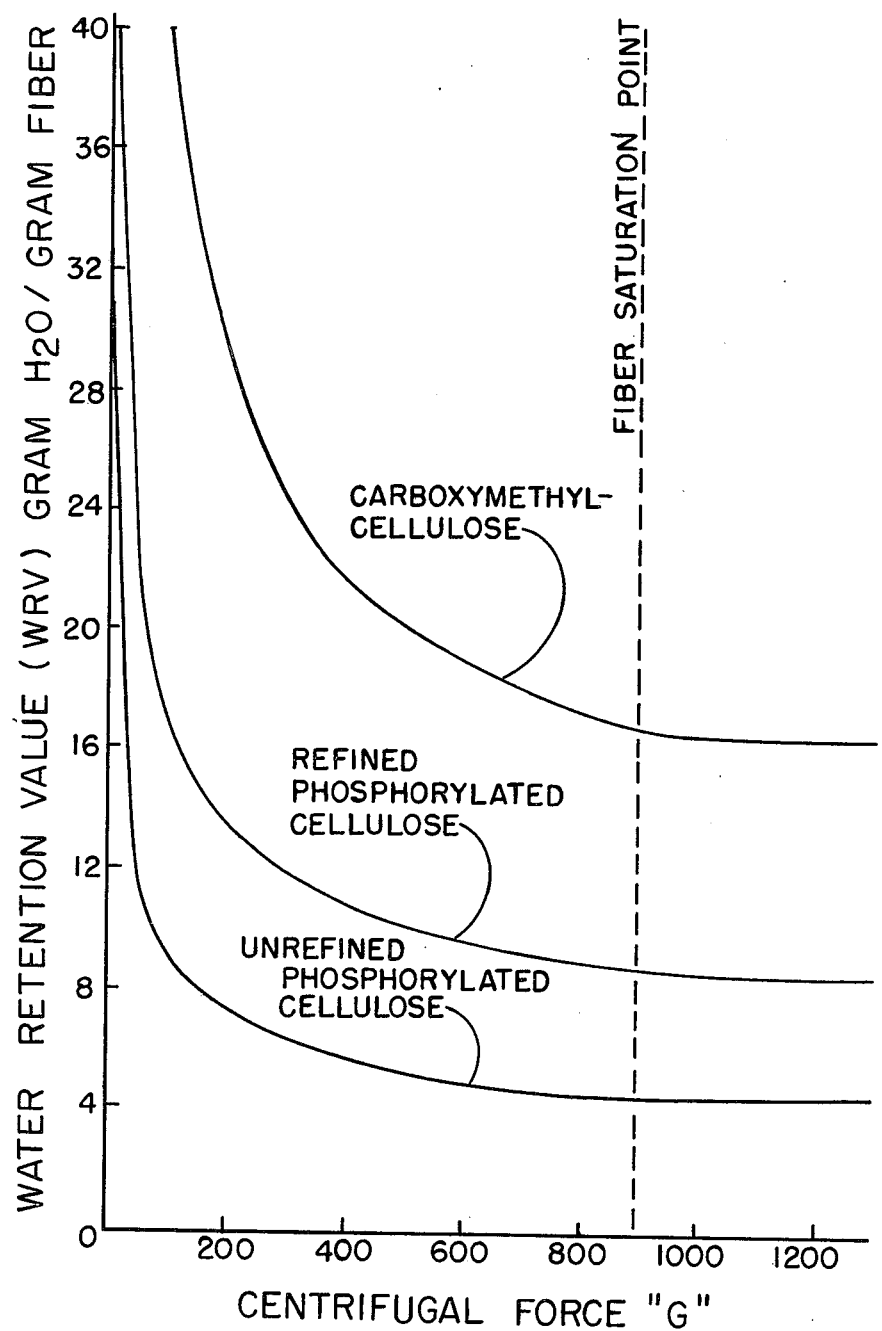
FIG. 26 illustrates fiber saturation points.

When dry cellulosic fibers are immersed in water, the water will penetrate into the fiber wall causing it to swell. The swelling will continue until the stresses within the fiber wall are in equilibrium with the capillary forces which tend to drive the water into the fiber wall. The water content of completely saturated fibers is calld the fiber saturation point ("FSP") and is commonly expressed in grams of water per gram of dry fibers. FIG. 26 illustrates the fiber saturation points of representative materials of the invention.

Thus, when fibers are immersed in water part of the water is contained within the fiber walls and the remainder is among the fibers and within the lumens. For the purpose of this discussion the water contained within the fiber walls is called internal water while the water outside the fibers is called external water. FIGS. 27 and 28 describe external and internal water contents for the representative materials including preferred ranges.

The most accurate method for determining the fiber saturation point is the solute exclusion technique. Dry fibers are immersed in an aqueous solution of a dextran of which the molecules are too large to penetrate into the capillaries of the fiber walls. Water is imbibed by the fibers excluding the solute. From the measured increase of the solute concentration of the ambient dextran solution, the weight of imbibed water i.e. the fiber saturation point can be calculated.

This method of determining the fiber saturation point is very laborious and it has been shown [Scallan and Carles, "Svensk Papperstidning" 75 (1972) (609–703)], that a very good correlation exists between fiber saturation point values as determined by the solute exclusion technique and the water retention values ("WRV") of most fiber samples after being subjected to a centrifugal force of 900 G's for one-half hour.

When by some chemical means hydrophilic groups are introduced onto the surface and within the amorphus regions of cellulosic fibers (e.g. phosphorylation) the fibers will absorb more water with a consequent increase in the fiber saturation point as described in the addendum to the above mentioned Scallan and Carles article. Beating and refining also increases the fiber saturation point of fibers. The fiber saturation point (or water retention value) of woodpulp fibers is rarely in excess of 2 grams/gram. For dried and reslushed pulp fibers the fiber saturation point is not larger than one gram/gram.

The fiber saturation points of some chemically modified hydrophilic fibers are shown in Table 3.

Table 3

| Material | FSP Gram/Gram | External Water Gram/Gram at 5% Consistency |
|---|---|---|
| Phosphorylated Fiber (unbeaten) | 4.5 | 14.5 |
| Phosphorylated Fiber (beaten) | 8.5 | 10.5 |
| Carboxymethyl cellulose (Aqualon - R) (unbeaten) | 16.5 | 2.5 |
| Woodpulp (average) | 1.5 | 17.5 |

Data in Table 3 shows that the chemically modified fibers contain more internal water (higher fiber saturation point) than the woodpulp fibers. Thus, at e.g. 5% consistency (95 grams water/5 grams of fibers) the quantity of external water varies with the fiber saturation point as is shown in Table 3, second column.

Because of the different amounts of external water, Aqualon R at 5% consistency is a gel with plastic characteristics while woodpulp is a free flowing slurry. The phosphorylated fibers have properties in between these two extremes.

The webs formed in accordance with the invention are characterized by a structure having an airy, mat-like appearance with (1) high absorbency, (2) controllable wicking or distribution properties, (3) controllable dry strength properties which can vary from a fluff-like mat to a soft, tissue-like sheet to a tough, flexible foam-like sheet and (4) controllable wet strength.

The present invention thus provides an improved highly absorbent material and process for making it having the following advantages:

1. No solvent drying is needed to retain the wicking and absorbent characteristics of the highly absorbent fibers—this produces a significant cost savings;

2. Internal fiber bonding is easily controlled within the webs by regulating the amount of hydrogen bonding between individual fibers in the drying stage with the following results:
    (a) by minimizing external water in sprayed fibers, the collected fibers form a bulky, loosely-bound mat of physically entangled fibers;
    (b) by partially drying all fibers before the collecting surface and subsequently drying them on the collecting surface, an airy mat of tacked fibers is formed with high strength, flexibility, and softness;

3. A means is provided for incorporating granular materials;

4. The liquid capacity of the web includes the increased interfiber capillary capacity as well as the swelled fiber capacity;

5. The fibers can be aligned or randomized by varying the angle of the spray pattern in relation to the collection surface with the following results:
    (a) by spraying directly downward toward the collecting surface the fibers are randomized in orientation;
    (b) by spraying on a sharp angle to the collecting surface the majority of the fibers are oriented in the spray direction;

6. When using an extrudate containing phosphorylated fibers, the flame retardant properties are particularly attractive for spray drying in heated air without flash fire danger.

The process of the invention is susceptible to various modifications including spraying extrudable fibers into a high velocity heated air stream such as a through dryer nozzle and collecting the dried fibers on a continuous wire to produce a new web in-line, spraying extrudable fibers onto a continuous collecting surface and drying the structure in a through dryer to produce a new web in-line, and spraying extrudable fibers into a heated cyclone, flash drying them, and collecting them onto a continuous surface to produce a new web in-line.

The process of the invention can also be used to integrate mechanically various materials with the highly absorbent fibers. For example, pre-mixing the materials into the extrudate and spraying this into a high velocity heated air stream such as through dryer nozzle and collecting the dried fibers on a continuous wire will produce an integrated web. Spraying extrudable fibers into one side of a high velocity heated air stream such as a through dryer nozzle and blowing picked roll pulp, for example, fibers into the other side of the high velocity heated air stream and collecting the integrated dried fibers on a continuous wire will produce an all air formed web in-line. Spraying extrudable fibers into a heated cyclone, flash drying them, blowing them through the blower unit of a roll pulp picker unit while picking a roll of pulp and collecting the integrated dried fibers on a continuous wire will produce an integrated web in-line. Spraying extrudable fibers into a melt-blowing process as described, for example, in U.S. Pat. No. 3,849,241 to Buntin et al will simultaneously dry and integrate the highly absorbent fibers into the melt blown web utilizing high velocity heated air of the melt blown process.

These and other examples of the present invention will be apparent to those skilled in the art. The foregoing are illustrative of the highly absorbent, airy mat-like structures which can be produced in accordance with the invention by controlling the interfiber bonding during air drying. There are numerous possibilities for producing new highly absorbent webs in accordance with the invention in a continuous manner for use as a component for end use products. The highly absorbent benefits can be utilized such as in sanitary napkins, tampons, disposable diapers, wipers, and other like products.

Thus, it is apparent that there has been provided in accordance with the invention a process for producing highly absorbent webs and resulting materials that fully satisfy the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications and variations as fall within the spirit and broad scope of the appended claims.

I claim:

1. Method of forming a highly absorbent web comprising the steps of;
   (a) forming a gel by mixing with a solvent chemically modified cellulose fibers selected from the group consisting of,
      (i) cellulose that has been subjected to chemical substitution, etherization or esterification,
      (ii) cellulose that has been subjected to chemical substitution, etherization or esterification and crosslinked, and
      (iii) cellulose that has been polymeric grafted, without dissolving said fibers to the extent that they are not identifiable,
   (b) removing from said gel mixture external solvent to the extent that the total amount remaining is within the range of ±5 grams per gram of fiber of the fiber saturation point,
   (c) spraying said gel mixture to separate said fibers,
   (d) collecting said fibers as sprayed into a web having a high degree of "z" direction fiber orientation, and
   (e) drying said fibers.

2. The method of claim 1 wherein the solvent is water and the fibers are selected from the group consisting of;
   (a) phosphorylated pulp,
   (b) acrylonitrile grafted pulp, and
   (c) cross-linked carboxymethyl cellulose.

3. The method of claim 2 wherein the fibers are phosphorylated pulp.

4. The method of claim 1 further including the step of refining said fibers prior to mixture with the solvent.

5. The method of claim 1 wherein the gel mixture is sprayed into a gas stream to increase the rate of drying.

6. The method of claim 5 wherein the gas stream is heated air.

7. The method of claim 1 further including the step of pattern bonding said formed web.

8. The method of claim 1 further including forming said web on a reinforcing web.

9. The method of claim 1 further including the step of adding a granular material to the sprayed fibers prior to final drying.

10. A spray formed, soft, highly absorbent web of chemically modified cellulose fibers selected from the group consisting of;
    (a) cellulose that has been subjected to chemical substitution, etherization or esterification,
    (b) cellulose that has been subjected to chemical substitution, etherization or esterification and cross-linked, and
    (c) cellulose that has been polymeric grafted,
wherein said fibers have substantial "z" direction orientation being formed from a gel having an external solvent content within a range of ±5 grams per gram fiber of the fiber saturation point.

11. The web of claim 10 wherein said fibers are selected from the group consisting of,
    (a) phosphorylated pulp,
    (b) acrylonitrile grafted pulp, and
    (c) cross-linked carboxymethyl cellulose.

12. The web of claim 11 wherein said fibers are phosphorylated pulp.

13. The method of claim 1 wherein the amount of external solvent remaining prior to spraying is ±3 grams per gram of fiber of the fiber saturation point.

14. The web of claim 10 wherein said gel has an external solvent content of ±3 grams per gram of fiber of the fiber saturation point.

* * * * *